United States Patent [19]

Auth et al.

[11] Patent Number: 5,695,507

[45] Date of Patent: Dec. 9, 1997

[54] TRANSLUMINAL THROMBECTOMY APPARATUS

[75] Inventors: David C. Auth, Kirkland; Thomas J. Clement; Lucas S. Gordon, both of Redmond, all of Wash.

[73] Assignee: Boston Scientific Corporation Northwest Technology Center, Inc., Redmond, Wash.

[21] Appl. No.: 617,259

[22] Filed: Mar. 18, 1996

Related U.S. Application Data

[62] Division of Ser. No. 317,229, Oct. 3, 1994, abandoned.

[51] Int. Cl.$^6$ ............................................. A61B 17/32
[52] U.S. Cl. ............................................. 606/159; 604/22
[58] Field of Search ............................ 606/159, 170, 606/180; 604/96

[56] References Cited

U.S. PATENT DOCUMENTS

| | | | |
|---|---|---|---|
| 4,994,067 | 2/1991 | Summers | 606/159 |
| 5,078,722 | 1/1992 | Stevens | 606/159 |
| 5,226,909 | 7/1993 | Evans et al. | 606/159 |
| 5,300,025 | 4/1994 | Wantink | 604/96 |
| 5,449,372 | 9/1995 | Schmaltz et al. | 606/198 |

*Primary Examiner*—Michael Buiz
*Assistant Examiner*—Patrick W. Rasche
*Attorney, Agent, or Firm*—Cowan, Liebowitz & Latman, P.C.

[57] ABSTRACT

The invention is an apparatus for breaking up a thrombus by introducing a rotating core wire into the thrombus whereby the fibrin of the thrombus will be withdrawn from the thrombus into the rotating core wire, thereby breaking up the network of the thrombus which prevents blood flow. The apparatus includes a drive shaft housing which can be used to withdraw fluid from the area of the thrombus or to introduce medicines, such as streptokinase which will further break up the thrombus or other chemicals such as contrast agents for visualizing the vascular anatomy. The apparatus also includes a shaft housing which is provided with an expanded catheter funnel at the distal end and a venturi insert immediately proximal to the distal end. The apparatus further includes a prime mover which, in addition to rotating the drive shaft, allows for axial motion of the drive shaft relative to the drive shaft housing.

18 Claims, 3 Drawing Sheets

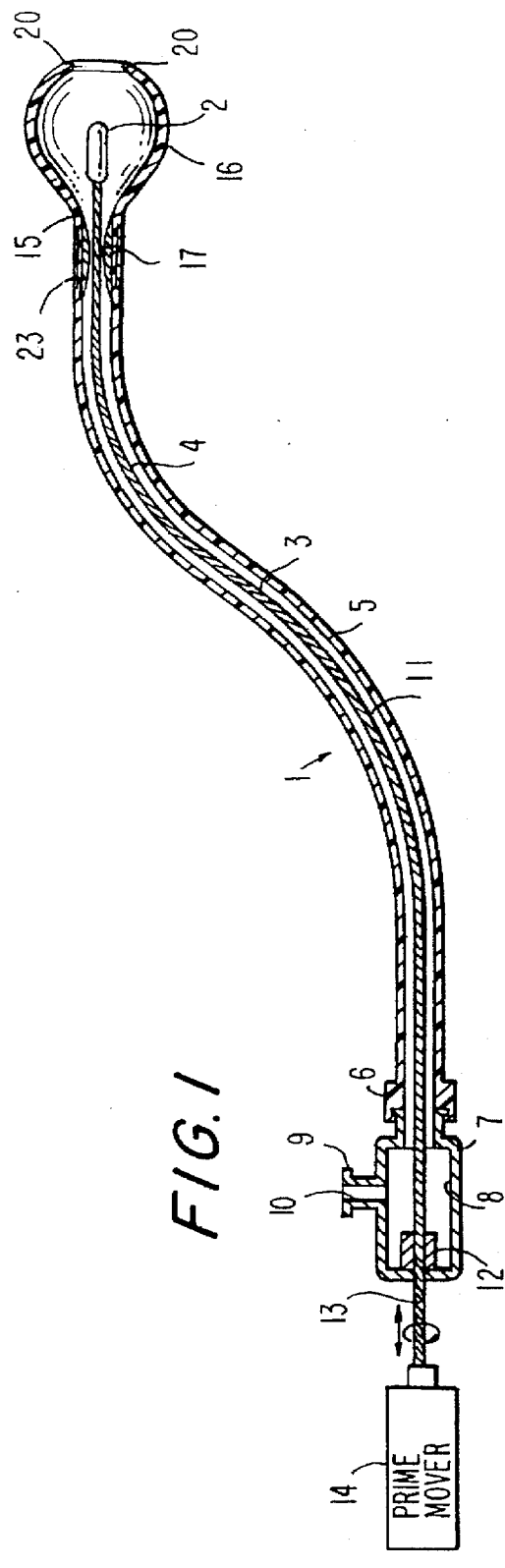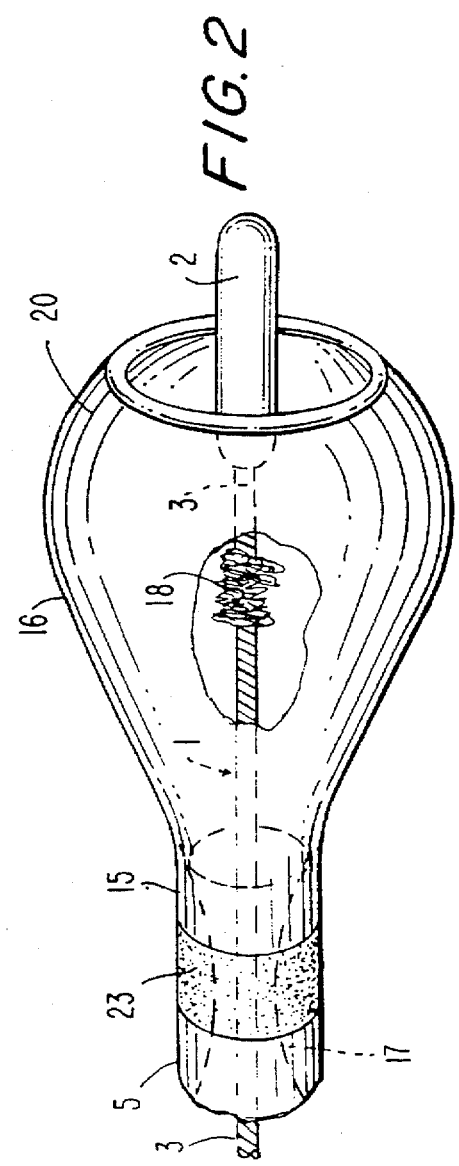

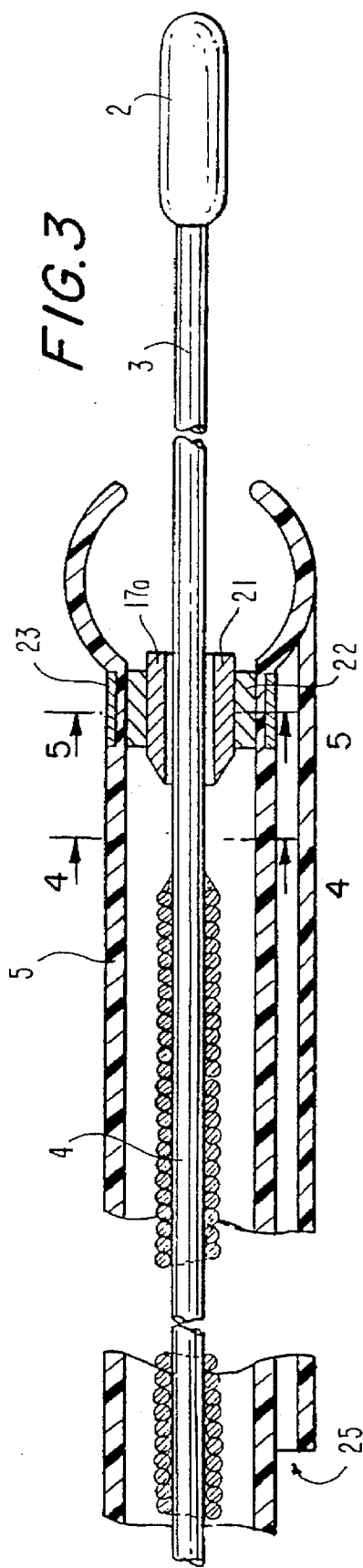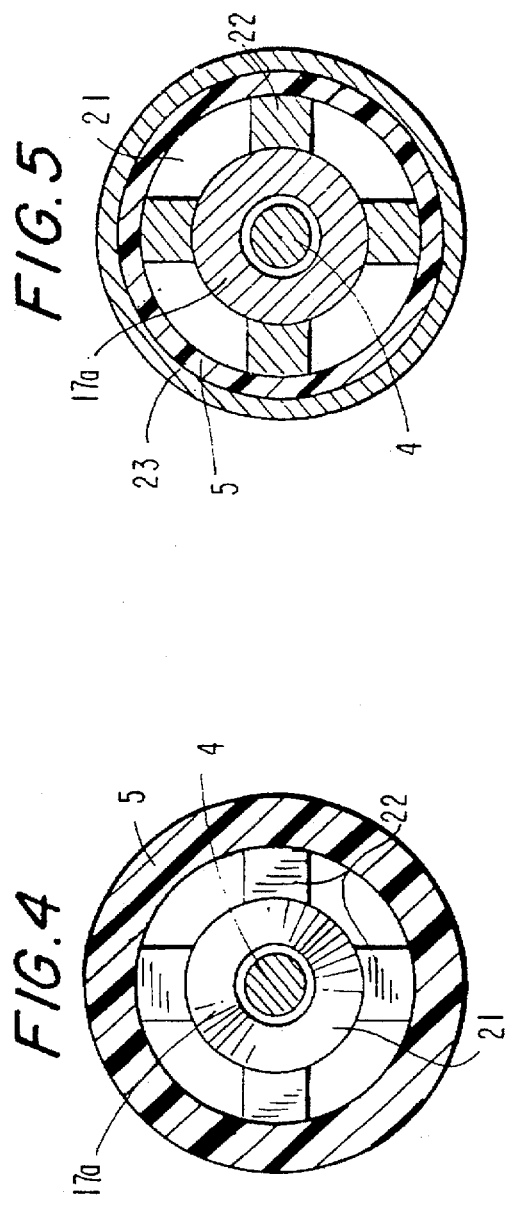

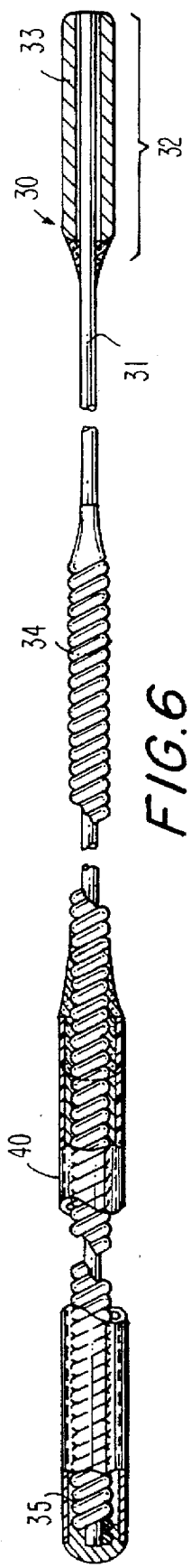
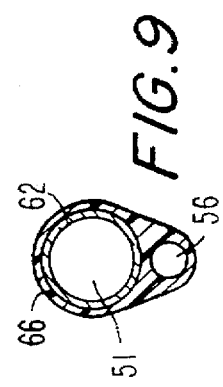
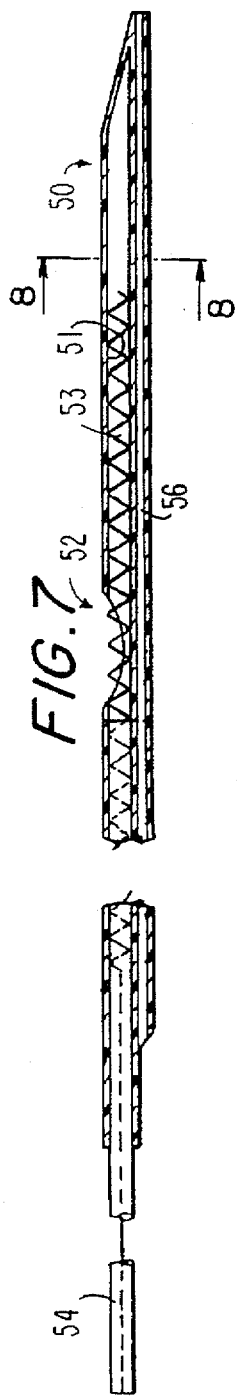
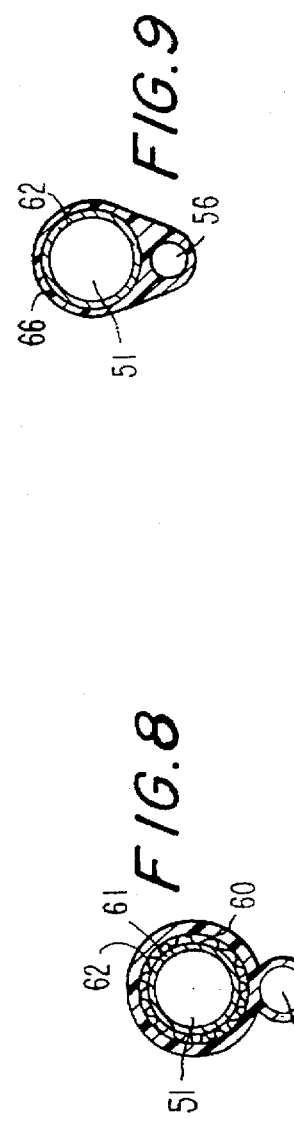

TRANSLUMINAL THROMBECTOMY APPARATUS

This application is a divisional of application Ser. No. 08/317,229, filed Oct. 3, 1994 now abandoned.

FIELD OF THE INVENTION

This invention relates to a device used to break up blood clots or thrombi which form within arteries. More particular, this invention relates to a device adapted to break up clots or thrombi which may form within a coronary artery.

BACKGROUND OF THE INVENTION

Approximately 1.2 million Americans suffer heart attacks each year. A large percentage of the heart attacks are caused by blood clots or thrombi which form within the coronary arteries. A thrombus is nature's way of stemming the loss of blood from its pipeline system by corking off an opening into the vascular tree. The biochemical process which results in thrombus formation is not fully understood. However, in simple terms, injury to the vascular wall releases chemicals which lead to conversion of soluble circulating fibrinogen molecules into a polymeric structure of fibrin. The fibrin structure is insoluble and arranges itself into a three dimensional network of meshed strands which entrap red blood cells. The individual strands are approximately 0.2 microns in diameter and the mesh size is approximately 1 micron. Accordingly, five micron red blood cells are easily trapped within the three dimensional "net".

When a thrombus forms, it effectively stops the flow of blood through the zone of formation. This is how the body normally protects itself from blood loss. If the thrombus extends across the interior diameter of an artery, it cuts off the flow of blood through the artery. If one of the coronary arteries is 100% thrombosed, the flow of blood is stopped in that artery resulting in a shortage of oxygen carrying red blood cells to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can nevertheless trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent (myocardial infarction). If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Coronary artery bypass graft (CABG) surgery is a surgical method for bypassing coronary arteries which, because of narrowing or obstruction, are unable to supply adequate oxygen to heart muscle. In recent years, direct administration of chemical lysing agents into the coronary arteries has been shown to be of some benefit to patients who have thrombosed coronary arteries. In this procedure, a catheter is placed immediately in front of the blockage and a drip of streptokinase or other lysing agent is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of small diameter branches.

Auth, U.S. Pat. No. 4,646,736, discloses a thrombectomy device that permits rapid removal of an obstructive thrombus. However, the device is characterized by small catheter tip size and thus is unable to remove large clots, except by the use of multiple rotating wires. Also, a clot which is not in good position of purchase on a vessel wall in the "line of fire" of the rotating wire is not fibrinectomized. This is especially true of clots floating freely in the blood stream, since it is virtually impossible to revolve within these clots in the absence of a constraint.

Further disadvantages which have been found in using the prior art thrombectomy device include the difficulty in maintaining the clot in the space about the wire during all degrees of rotation. In fact, sweeping out an entire arterial lumen with a rotating wire is virtually impossible in all but the smallest, i.e., less than 1.5 mm diameter, lumens. An additional disadvantage is that fragments of the clot which are not completely removed may be embolized downstream.

Therefore, there has been a definite need for a thrombectomy device that can be more effective in sweeping arteries, in fibrinectomizing clots that are free floating or not perfectly positioned, and in minimizing fragmentation of clots.

SUMMARY OF THE INVENTION

The present invention is an improved transluminal thrombectomy apparatus. It comprises a flexible drive shaft over a small diameter core wire, having a tip affixed thereto, where the tip is an elongated cylinder with rounded ends and has a diameter which is greater than the diameter of the core wire. The apparatus further comprises a flexible, cylindrical shaft housing having a venturi insert adjacent its distal end and an outwardly expanding catheter funnel. The shaft housing, which extends along and surrounds the drive shaft, may optionally have one or more sharp-edged members concentric to the core wire. The device includes connecting means for sealably connecting the end of the shaft housing which is remote from the tip to an apparatus capable of providing a fluid path through the drive shaft housing to the end of the drive shaft housing at which the tip is located. The device includes means for generating negative pressure in the fluid path at the proximal end of the drive shaft housing to induce suction of clot into the rotating core wire at the remote end of the drive shaft housing. In addition, the device includes drive shaft connecting means at the end of the drive shaft which extends through the shaft housing connecting means for connecting the drive shaft to a rotating prime mover.

In another embodiment of the invention, the transluminal thrombectomy apparatus comprises a flexible catheter having a closed distal end and defining a lumen wherein there is a lateral opening proximal to the distal end. A coil extends from a drive shaft longitudinally through said lumen and is oscillated and/or rotated, such that fibrin collects around the distal portion of said coil through the distal lateral opening in the catheter.

The drive shaft connecting means allows for longitudinal motion of the drive shaft/core wire relative to the cylindrical shaft housing. Longitudinal motion of the drive shaft/core wire may be in the forward or rearward direction, during rotation of the drive shaft/core wire or when the drive shaft/core wire is not rotating. Longitudinal motion of the drive shaft/core wire may be mechanically driven in an oscillatory fashion with a predetermined excursion amplitude, or it may be achieved manually by the device operator.

BRIEF DESCRIPTION OF THE DRAWINGS

FIG. 1 is a cross-sectional pictoral view of an embodiment of the present invention;

FIG. 2 is a plan view of the distal end of a preferred embodiment of the invention;

FIG. 3 is a cross-sectional view of the distal end of an embodiment of the invention;

FIGS. 4 and 5 are each a lateral cross-sectional view along line 4—4 in FIG. 3;

FIG. 6 is a cross-sectional segmental view of a core wire useful according to the invention;

FIG. 7 is a cross-sectional pictoral view of another embodiment of the invention; and FIGS. 8 and 9 are each a lateral cross-sectional view along line 8—8 in FIG. 7.

DETAILED DESCRIPTION OF THE INVENTION

FIG. 1 illustrates a transluminal thrombectomy apparatus 1 of the present invention. The device 1 preferably includes an elongated, cylindrical atraumatic tip 2 having rounded ends which is rotated by a transluminal core wire 3. The core wire 3 is supported over the majority of its length by a flexible helical drive shaft 4, which is bonded or affixed to core wire 3 at one or more places. The drive shaft 4 is contained within a flexible shaft housing 5 which is typically made of a plastic material. The inside diameter of the shaft housing 5 is preferably selected to be greater than the diameter of the tip 2 in order that the tip 2 can be withdrawn into the shaft housing 5. At the end of the shaft housing 5 remote from the tip 2 there is preferably a shaft housing connector 6 which may be used to quickly connect the shaft housing 5 to a drive shaft bearing block and shaft seal 7. The shaft housing connector 6 permits rotation of the shaft housing 5, as will be discussed more below.

The drive shaft bearing block and shaft seal 7 is a body which has a central cavity 8 and a port 9 connected thereto. The port 9 also includes a quick connect fitting 10 in order that a fluid path exists from the port 9 through the central cavity 8 and through the interior lumen 11 of the shaft housing 5. This fluid path can be used either to withdraw fluid through the shaft housing 5 by vacuum or suction or to dispense drugs, such as streptokinase, or otherwise infuse fluid, through the shaft housing 5.

A fluid seal 12 which allows rotational and axial movement of the drive shaft 4 is at one end of the drive shaft bearing block and shaft seal 7. The proximal end 13 of the drive shaft 4 remote from the tip 2 is connected to a rotary prime mover 14.

The distal end 15 of the shaft housing 5 is connected to an expanded catheter funnel 16. Immediately adjacent to the catheter funnel 16 the distal end 15 of shaft housing 5 is provided with a venturi insert 17, as shown in FIG. 2. The catheter funnel 16 is preferably provided with atraumatic edge curls 20 to minimize traumatization of the arterial walls. The venturi insert 17 serves to provide wire support, clot focusing, fibrin compaction and collection functions, which enhances the overall efficacy and efficiency of the device.

Optionally, as shown more clearly in FIGS. 3 to 5, an insert 17a may comprise one or more knife members, i.e., sharp-edged, or knife-like members, 21 positioned on support members 22 substantially concentrically to core wire 3. The purpose of members 21 which may have sharp edges located proximally, distally, or both, is to remove collected matter from the core wire.

A preferred core wire 30 is shown in FIG. 6, where the primary wire 31, which is hollow or, preferably, solid, extends the length of core wire 30. The distal portion 32 of core wire 30 comprises a solid annular member 33 that is affixed, such as soldered, welded, or glued, to the distal part of primary wire 31, and said solid tip is preferably comprised of a radiopaque alloy or metal such as platinum. Proximal to said distal portion 32 the core wire 30 comprises only the wire itself, until a spring coil 34 surrounds said core wire 30 and extends proximally to the proximal end 35 of core wire 30. Preferably the proximal portion of core wire 30 functions as a drive shaft and contains a metal hypotube 40 concentrically surrounding coil 34. The metal hypotube 40 preferably extends distally less than the entire length of primary wire 31. Solder or glue or other suitable affixation means can be used at the proximal end 35 of core wire 30, the distal end of hypotube 40, and the distal end of coil 34.

In operation, the rotating tip 2 is pushed through a thrombus. When the core wire/drive shaft wire (3 and 4) are rotated, fibrin 18 is wound around the small core wire shaft 3 (see FIG. 2). This happens because of friction between the fibers and the surface of the rotating core wire 3 and because of a localized "whirlpool" in any free liquid surrounding the tip 2 and the core wire 3. As the fibers 18 follow about the rotating core wire 3, their tension increases, further tightening their grip on the core wire 3 and eventually stripping away an interior volume of the fibrin network. Red blood cells which were entrapped can be released back into the circulatory system without emboli-producing large fragments, since the insoluble material is retained on the core wire 3 for later extraction from the body.

As shown in FIG. 2, the fibrin 18 winds around the core wire 3, when the core wire is rotating. Since the fibrin 18 winds very tightly around the core wire 3, and since the fibrin 18 constitutes only about 4% of the volume of the thrombus, it is possible to strip the clot's framework and thereby eliminate a large volume of the clot before the core wire 3 of the thrombectomy apparatus 1 needs to be withdrawn from the patient for cleaning or replacement. The device additionally provides suction through the fluid path defined by the drive shaft housing which pulls more clot into the rotating wire. In many cases, the entire thrombectomy can be performed without using up the fibrin storage capacity of the core wire 3.

Consistent with FIG. 1, the tip 2 can comprise a generally sausage-shaped, preferably radiopaque piece affixed to a cylindrical metal core wire 3. The rounded edges of the front and rear of the tip 2 reduce the probability of inadvertent perforation of vessel walls and the thin core wire 3 provides torque transmission as well as an area for coiling and storing the fibrin.

In the preferred embodiment of the invention, the tip 2 has a diameter of about 16 mils (0.016 inch) and a length of about 60 mils, and it is mounted on a 5 mil stainless steel core wire 3. As will be understood by those skilled in the art, it could be advantageous to have tips with diameters as small as 10 mils to negotiate very tiny arteries and narrowing segments. In such cases, the core wire 3 would be proportionately smaller or compliant to the tip 2 to avoid ram puncture of an artery.

While the tip 2 of the preferred embodiment 1 is an oblong cylinder with rounded ends, a tip of spherical or otherwise symmetrical shape could also be used. In the preferred embodiment 1 of the invention, the tip 2 is made of a radiopaque material, such as platinum, and it is attached to the core wire 3 by gluing or welding or soldering. When viewed angiographically, the elongated sausage shape of the tip 2 is quickly visualized with its axis clearly defined. Having an elongated geometry facilitates localization on raster scanned video displays.

To provide angiographic surveillance of the end of the drive shaft housing 5, a special marker 23 is preferably affixed to the distal end of the shaft housing 5. The marker 23 is also made radiopaque by fabricating it from solid platinum or a platinum alloy or from gold, or by molding, preferably from a radiopaque-filled plastic. In a preferred embodiment, the marker 23 is machined from platinum and glued and/or crimped to the shaft housing 5 and/or it is positioned concentric to knife members 21. The marker 23 has been visualized under an angiography machine along with the platinum sausage shaped tip 2, so there is an extremely clear and easily read image of the respective components 2, 20.

With reference to FIG. 2, the core wire 3 of a preferred embodiment of the present invention is comprised of a 5 mil stainless steel core wire. Alternatively, a core wire consisting of a small (approximately 0.003 inch) gold wire helically wound around a straight stainless steel wire of approximately 0.004 inch could be used. Since flexibility is improved by using a helical wire lay-up, it may be advantageous in reducing perforation of the vessel wall by, in effect, having a "softer" tip 2 for a given diameter core wire 3. Deliberate roughening of a solid core wire, or adjusting the spacing of the helical lay-up on the composite core wire 3, might be desirable in some clinical applications where fibrous material is more resistant to coiling and capture. The core wire 3 is wrapped with a stainless steel helical drive 4 to add support and strength for handling and manipulating the wire. Approximately 2 inches of core wire 3 are exposed between the drive shaft 4 and the tip 2. As shown in FIGS. 3 and 6, drive shaft 4 is preferably affixed to core wire 3 by solder.

As described above, in the preferred embodiment the drive shaft 4 is housed in a tubular shaft housing 5 which can be used as a conduit for infusion of fluids, including those that aid thrombolysis. It can also be used to monitor pressure or suck the thrombus or clot onto the rotating core wire 3 and up the shaft housing 5.

In an optional embodiment of the invention the distal portion of the device 1 may have a limited, longitudinally extending channel, such as lumen 25 in FIG. 3. Such a channel is useful for tracking in "monorail" fashion over a preferably steerable guidewire. The channel would preferably be from about 5 to 25 cm, more preferably from about 15 to 25 cm, in length.

In order to use the device 1, the drive shaft 4, core wire 3, and tip 2 are rotated by a prime mover 14 at a speed which is preferably in the range of 500 to 6000 rpm for coiling of fibrin. Higher speeds may be used, but they are unnecessary. If the speed is reduced too much, the advantage of "orthogonal displacement" of longitudinal friction is lost. If the tip 2 is advanced without rotation into the thrombus, it will, if advanced very slowly, have a tendency to jerk forward due to friction force on the drive shaft/housing and frictional forces on the tip/thrombus interface. Without rotation and with steady longitudinal advance, the dynamic coefficient of friction will govern the force required through the catheter and into the thrombus.

The addition of rotation to the drive shaft 4 and tip 2 results in adjusting the friction vector away from the longitudinal direction toward the circumferential direction. Since the magnitude of the dynamic coefficient of friction is normally quite constant, independent of velocity, the magnitude of the total friction vector is essentially constant. With a constant magnitude of friction, the more rotational speed imparted to the drive shaft 4 and tip 2, the more the friction vector is adjusted away from the longitudinal direction. The result is a reduction of longitudinal force required to slide in the longitudinal direction. This diminishes the force required to push the catheter along the shaft housing 4 and the force required to penetrate a thrombus. With less force required to advance the tip 2, less distention and bowing of the drive shaft 4 and shaft housing 5 will result when penetrating a thrombus. Also less force will be required by the physician at the point of percutaneous entry.

With respect to a representative drive shaft 4 having diameter of 0.2 mm (corresponding to 0.008" or 8 mils) the RPM required to have a circumferential component of velocity equal to a typical longitudinal advance velocity of 10 mm per second is:

$$RPM = \frac{10 \text{ mm/sec}}{(.2 \text{ mm})(\pi)} \times 60 \text{ sec/mm} = 955 \text{ RPM}$$

With the assumption of isotropic coefficients of friction for orthogonal directions of slip, this implies a longitudinal friction force equal to a circumferential friction force or a reduction of longitudinal friction by about 30%. In this same example, the fibrin forms a helix around the drive shaft with a pitch of one part in one or 45°. This implies engagement of a large amount of fibrin network per single rotation and hence an increase in the amount of torque required to break the fibrin fibers away from their radially more distant neighbors. Operation at 4000 RPM has been shown to reduce total torque required to a low level for a typical advance rate of approximately 10 mm per second and to provide a good target RPM for general applications. At 4000 RPM, the orthogonal displacement of longitudinal friction is more than 75% in the above example, thus reducing force required in the longitudinal direction to less than 25% of its non-rotating level. Of course, parts of the system with larger radii of gyration will experience an even larger reduction in the amount of longitudinal force required vis-a-vis the non-rotating case.

The device 1 is generally operated in one of two different modes. In the first mode, a commercial angioplasty guide wire is advanced across the region containing thrombus using standard techniques employed by angiographers. The shaft housing 5 is then loaded over the standard guide wire until the radiopaque marker is located adjacent to the thrombus. The commercial guide wire is removed from the shaft housing 5 and the thrombectomy wire (tip 2, core wire 3, and drive shaft 4) is loaded through the drive shaft housing 5 until the tip 2 is located beyond the thrombus and therefore the core wire 3 is located in the thrombus. The drive shaft housing connector 6 and drive shaft 4 are then attached to the prime mover 14. Suction is applied to the fluid path simultaneous with rotation of the thrombectomy wire—coaxing the thrombus into the rotating core wire 3 and wrapping the fibrin from the clot onto the core wire 3. The rotating core wire 3 can be advanced or retracted to expose new areas of the core 3 to further fibrin winding.

In the second mode of operation, the core wire 3 and tip 2 are preformed into a gentle bend. The thrombectomy wire (tip 2, core wire 3, and drive shaft 4) are then steered into position with the tip 2 located beyond the thrombus using standard wire placement techniques used by angiographers. Once the tip 2 is located beyond the thrombus, the drive shaft housing 5 is placed over the thrombectomy wire, and the drive shaft housing connector and drive shaft 4 are attached to the prime mover 14. The procedure then continues as described above.

In a preferred embodiment of the invention the rotating thrombectomy apparatus is moved axially, distally or proximally, manually or mechanically. This axial movement can optionally be synchronized with the rotation. The axial movement may be oscillatory with a predetermined excursion amplitude, optionally in conjunction with the rotation. Due to the addition of longitudinal or axial oscillation while the device is rotating in the fibrin winding mode, the funnel will function to position the clot with fibrin structure against the drive shaft while at the same time longitudinal excursions will allow clot and fibrin to pass through the orifice of the funnel into the suction retrieval portion of the catheter. This may be combined with blades pointed in the proximal direction at the general location of the funnel orifice to strip fibrin from the shaft to thereby denude it and make the apparatus more receptive to further fibrin winding.

As with prior art devices, the device of the present invention may also be made steerable by preforming the distal segment of the shaft housing immediately before the outwardly expanding catheter funnel to create a gentle arched region. Rotation of the entire shaft housing by the angiographer will then serve to point the distal segment of the shaft housing in a given off-axis direction.

Such steerability may be coupled with a core wire which is straight or preformed to have its arch (not shown) potentially overlapping that of the shaft housing. When such overlap occurs, the system resists rotation of the drive shaft since the two bends are in synchrony with each other. When the system is forced to rotate, the relative time spent with an angular orientation such that the bends coincide is greater than that spent when they are in opposition. The angiographer may therefore steer the system into a desired branch vessel by rotating the shaft housing to point in the direction of the desired branch. A swivel connector facilitates rotation of the shaft housing. Since the system spends more time in the angular position with preformed arches overlapping, the tip will have an enhanced probability for entering the desired branch vessel as it is advanced, provided the steering is correct.

The device 1 has been described for use in coronary thrombectomies. Other uses, such as the endoscopic removal of clots from the stomach or other cavities via transmission through the operating channel of the endoscope and the removal of other abnormal intracorporeal fibrous mass or fiber reinforced mass, are additional applications for the device. These and other applications will be apparent to one skilled in this art.

Another embodiment of the invention is shown in FIGS. 7 to 9, where a flexible catheter 50 has a longitudinally extending lumen 51 and a lateral opening 52. A flexible, shaped wire or coil 53 extending through lumen 51 is caused by drive shaft 54 to rotate and/or oscillate. A negative pressure within lumen 51 and/or the movement of the shaped wire 53 causes thrombus (not shown) to enter opening 52 where it engages coil 53.

Catheter 50 may optionally have a second, shorter lumen 56 which may extend partially or the entire length of catheter 50. Lumen 56 is open at its proximal and distal ends and may be useful for advancing catheter 50 over, for example, a guidewire (not shown). Preferably the distal end of lumen 56 is adjacent the distal end of lumen 51 and the proximal end of lumen 56 is substantially, from about 10 to 100 cm, distal to the proximal end of lumen 51.

Two possible cross-sectional configurations are shown in FIGS. 8 and 9. In FIG. 8, outer casing 60 defines lumens 52 and 56. Moreover, there is an inner wall 61 with braiding or other support material 62 in the space between casing 60 and inner wall 61. Also, the lower portion of casing 60 may optionally have a slit 63 for removing the device from a guidewire. In the variation shown in FIG. 9, casing 66 defines lumens 52 and 56, and the inner wall of casing 66 defining lumen 52 may have an inner tubular concentric member 62 for support. Member 62 could be comprised of suitable polymer material, flexible metal, such as stainless steel, or braiding comprised of polymeric or metal compounds.

Shaped wire 53 is preferably a helical coil where the pitch of the coil is from about 1 to 8 times, more preferably about 4 times, the mean diameter of the coil. The shaped wire 53 should be comprised of or having a coating of a material, for example, a polymer or metal, resistant to body fluids or corrosion in aqueous solutions. Preferred materials include metals resistant to corrosion, such as stainless steel, nitinol, or cobalt alloy MP35N, optimally radiopaque.

It will be further apparent to one skilled in this art that the improvements provided for in the present invention, while described with relation to certain specific physical embodiments also lend themselves to being applied in other physical arrangements not specifically provided for herein, which are within the spirit and scope of the invention taught here.

We claim:

1. A transluminal thrombectomy apparatus comprising:
   (a) a flexible catheter with proximal and distal ends and defining first and second elongated lumens each having an axis, the axis of each of said elongated lumens being spaced apart, said first lumen having an open proximal end, a closed distal end, a lateral opening proximal to its closed distal end and said second lumen having open proximal and distal ends;
   (b) a flexible, shaped wire extending through said first lumen and having proximal and distal ends, the distal end of the shaped wire extending distally to at least the lateral opening in said first lumen;
   (c) a drive means to which the proximal end of the shaped wire is attached;
   (d) suction means attached to the proximal end of said catheter and in communication with said first lumen; and
   (e) a guidewire with proximal and distal ends extending through said second lumen, the distal end of the guidewire extending distally of the distal end of said second lumen and the proximal end of the guidewire extending proximally of the proximal end of said second lumen.

2. The transluminal thrombectomy apparatus of claim 1, wherein the distal end of the shaped wire extends distally to the distal end of the first lumen.

3. The transluminal thrombectomy apparatus of claim 1, wherein said shaped wire is a helical coil.

4. The transluminal thrombectomy apparatus of claim 3, wherein said helical coil is comprised of a metal resistant to corrosion in aqueous solutions.

5. The transluminal thrombectomy apparatus of claim 3, wherein said helical coil is comprised of radiopaque material.

6. The transluminal thrombectomy apparatus of claim 3, wherein the pitch of said helical coil is from about 1 to 8 times the mean diameter of said helical coil.

7. The transluminal thrombectomy apparatus of claim 6, wherein the pitch of said helical coil is about 4 times the mean diameter of said helical coil.

8. The transluminal thrombectomy apparatus of claim 1, wherein said drive means includes a drive shaft means and a seal means, said drive shaft means extending through said seal means and connecting to said shaped wire, said seal means being adapted to permit rotational, axial, or rotational and axial movement of said drive shaft.

9. The transluminal thrombectomy apparatus of claim 1, wherein at least a portion of said catheter is made of a radiopaque material.

10. The transluminal thrombectomy apparatus of claim 1, wherein said second lumen is shorter than said first lumen and wherein the distal end of the second lumen is located adjacent the distal end of said catheter and the proximal end of the second lumen is located a substantial distance distal to the proximal end of said catheter.

11. The transluminal thrombectomy apparatus of claim 1, wherein the shaped wire is capable of being driven mechanically either proximally or distally, either synchronously with rotation or without.

12. The transluminal thrombectomy apparatus of claim 1, wherein the shaped wire is capable of being driven mechanically proximally and distally in an axial oscillatory fashion with a predetermined excursion amplitude either with or without simultaneous rotation.

13. A transluminal thrombectomy apparatus according to claim 1, wherein the drive is capable of both rotating and oscillating.

14. A transluminal thrombectomy apparatus according to claim 1, whereby thrombus is drawn into the lateral opening by the movement of the shaped wire.

15. A transluminal thrombectomy apparatus according to claim 1, whereby thrombus is drawn into the lateral opening by vacuum created by the suction means.

16. A transluminal thrombectomy apparatus according to claim 1, whereby thrombus is drawn into the lateral opening by a combination of the movement of the shaped wire and vacuum created by the suction means.

17. A transluminal thrombectomy apparatus according to claim 1, wherein the drive means is capable of rotating the shaped wire.

18. A transluminal thrombectomy apparatus according to claim 1, wherein the drive means is capable of oscillating the shaped wire.

* * * * *